United States Patent
Yurino

[11] Patent Number: 5,263,936
[45] Date of Patent: Nov. 23, 1993

[54] CONTINUOUS LOCAL ANESTHETIZATION SET

[76] Inventor: Masaki Yurino, 5-3-3829, Hishikagura 3-sen, Asahikawa-shi, Hokkaido, Japan

[21] Appl. No.: 755,859
[22] Filed: Sep. 6, 1991

[30] Foreign Application Priority Data
Jan. 30, 1991 [JP] Japan .................. 3-9306[U]

[51] Int. Cl.⁵ .......................................... A61M 5/178
[52] U.S. Cl. ..................... 604/158; 604/166; 604/164; 604/264
[58] Field of Search ................. 604/158–163, 604/264, 280, 283, 164–170

[56] References Cited

U.S. PATENT DOCUMENTS

| | | | |
|---|---|---|---|
| 3,856,009 | 12/1974 | Winnie | 128/214.4 |
| 4,650,472 | 3/1987 | Bates | 604/158 |
| 4,721,506 | 1/1988 | Teves | 604/158 |
| 4,973,312 | 11/1990 | Andrew | 604/158 |
| 4,994,036 | 1/1991 | Biscoping et al. | 604/158 |
| 5,100,390 | 3/1992 | Lubeck et al. | 604/158 |
| 5,106,376 | 4/1992 | Mononen et al. | 604/158 |

FOREIGN PATENT DOCUMENTS

| | | | |
|---|---|---|---|
| 0049856 | 4/1982 | European Pat. Off. | |
| WO90/14124 | 11/1990 | World Int. Prop. O. | |
| 9108785 | 6/1991 | World Int. Prop. O. | 604/158 |

Primary Examiner—C. Fred Rosenbaum
Assistant Examiner—Chalin Smith
Attorney, Agent, or Firm—Flynn, Thiel, Boutell & Tanis

[57] ABSTRACT

This invention relates to a continuous local anesthetization set to be used for setting a catheter in a spinal subarachnoid space, the continuous local anesthetization set consisting of a puncturing guide needle 2, a guide member 3 and a catheter 4, the puncturing guide needle 2 is known. The guide member 3 is composed of a guide pipe 3A, the diameter of which is substantially equal to that of a guide needle 2A1, and a knob 3B fitted firmly around a substantially intermediate portion of the outer circumferential surface of the guide pipe 3A, the guide member 3 being formed so as to be fitted detachably in the puncturing guide needle 2. The catheter 4 is provided at the front end section thereof with a curled pigtail-like portion 4A or inverted J-shaped portion 4A1, and it is inserted at the rear end 4B thereof into the front end 3A1 of the guide pipe 3A in the guide member 3, passed through the guide pipe 3A and then drawn out therefrom slowly, the pigtail-like portion 4A or an inverted J-shaped bent portion 4A1 being positioned in the front end portion 3A1 of the guide pipe 3A.

1 Claim, 5 Drawing Sheets

CONTINUOUS LOCAL ANESTHETIZATION SET

BACKGROUND OF THE INVENTION

1. Field of the Invention

This invention relates to medical instruments and, more specifically, to a continuous local anesthetization set to be used for setting a catheter in a place in the vicinity of a nerve for example, in a spinal subarachnoid space.

2. Description of the Prior Art

For example, the conventional catheters to be set in a spinal subarachnoid space include a catheter which is used by sticking a double needle, such as a epidural spinal anesthetic needle (Japanese Utility Model Application No. 41007/1988) having a Huber-pointed edge, or a spinal needle into the lumbodorsal skin from the rear side toward the spine (the tip of the needle reaches a spinal subarachnoid space through the skin, subcutaneous tissue, various kinds of ligaments and arachnoid membrane), pulling out an inner needle from the double needle, inserting this catheter into an outer needle which serves as a guide needle, and setting the catheter in the spinal subarachnoid space.

It is known that, when a catheter is stuck into a spinal subarachnoid space by using such a double needle, the patient has a post-spinal anesthesia headache which is ascribed to the leakage of a post-puncture medullary liquid from the puncture, and a rate of occurrence of this headache is proportional to the thickness of the needle. When the needle is thick, damage to the tissue in the punctured portion increases. Therefore, it is desirable that a very thin catheter be set in a spinal subarachnoid space by using a thin needle. However, when a catheter is made thin, it becomes soft and difficult to be inserted into a needle.

Under the circumstances, a catheter with a metallic stylet inserted therein has been used. Although this has enabled a catheter to be made rigid, the occurrence of bend of a catheter to be prevented, and the inserting of a catheter into a needle to be done easily, new problems have arisen.

For example, when a catheter is set in a spinal subarachnoid space, the front end thereof impinges upon a spinal wall or spinal cord, so that it becomes impossible to insert a catheter of a required length into a spinal subarachnoid space, and the degree of danger of compressing and hurting the spinal cord by the tip of a catheter increases. When the tip of a catheter impinges upon a spinal wall, the injection of an anesthetic cannot be sufficiently carried out. When a catheter is set in a one-sided state in a spinal subarachnoid space, an anesthetic is injected in only one direction, resulting in a partial anesthetization, even if the catheter setting operation itself is successfully carried out.

The above problems encountered in use of the conventional catheters are summarized as follows:

A. The opened free end portion of a catheter set in a spinal subarachnoid space impinges upon a spinal wall to prevent an anesthetic from being injected sufficiently into the spinal subarachnoid space.

B. A catheter of a required length cannot be inserted into a spinal subarachnoid space.

C. A catheter is set in a one-sided state, so that an anesthetic is injected into a spinal subarachnoid space partially, i.e., in one direction of the interior thereof, this causing the anesthetization effect to become partial.

SUMMARY OF THE INVENTION

In order to solve these problems, the continuous local anesthetization set according to the present invention is constructed as follows.

A continuous local anesthetization set comprising a puncturing guide needle 2, a guide member 3, and a catheter 4, the puncturing guide needle 2 consisting of a guide needle portion 2A, and a core portion 2B capable of being inserted into and withdrawn from the guide needle portion 2A, the guide needle portion 2A being composed of a guide needle 2A1 having an edge at the free end thereof, and a receiving portion 2A2 attached to the base end of the guide needle 2A1, the core portion 2B consisting of a core 2B1 capable of being inserted into and withdrawn from the guide needle 2A1, and a knob 2B2 attached to the base end of the core 2B1, the knob being formed so that it is detachably fitted in a receiving bore 2A21 provided in the rear end surface of the receiving portion 2A2, the guide member 3 consisting of a guide pipe 3A, the diameter of which is substantially equal to that of the guide needle 2A1, and a knob 3B fitted firmly around a substantially intermediate portion of the outer circumferential surface of the guide pipe 3A, the knob 3B being provided on the surface thereof which is on the side of a front end 3A1 of the guide pipe 3A with a front end portion 3B1 adapted to be detachably fitted in the receiving bore 2A21, the catheter 4 being dimensioned so as to be moved forward and backward freely through the guide needle 2A1 and the guide pipe 3A, the catheter 4 being provided at the front end section thereof with a curled pigtail-like portion 4A or an inverted J-shaped bent portion 4A1. The catheter 4 is previously prepared for an anesthetizing operation in such a manner that it is inserted at the rear end 4B thereof into the front end 3A1 of the guide pipe 3A in the guide member 3, passed through the guide pipe and then drawn out therefrom slowly, the pigtail-like portion 4A or the inverted J-shaped bent portion 4A1 being positioned in the front end portion of the guide pipe 3A.

BRIEF DESCRIPTION OF THE INVENTION

DETAILED DESCRIPTION OF THE PREFERRED EMBODIMENTS

Figure 1:
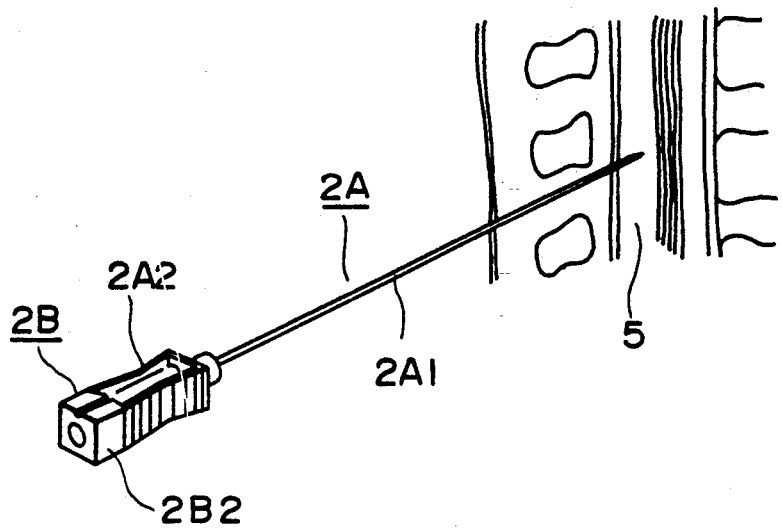
FIG. 1 is a perspective view illustrating the condition of use of a puncturing guide needle.
Figure 2:
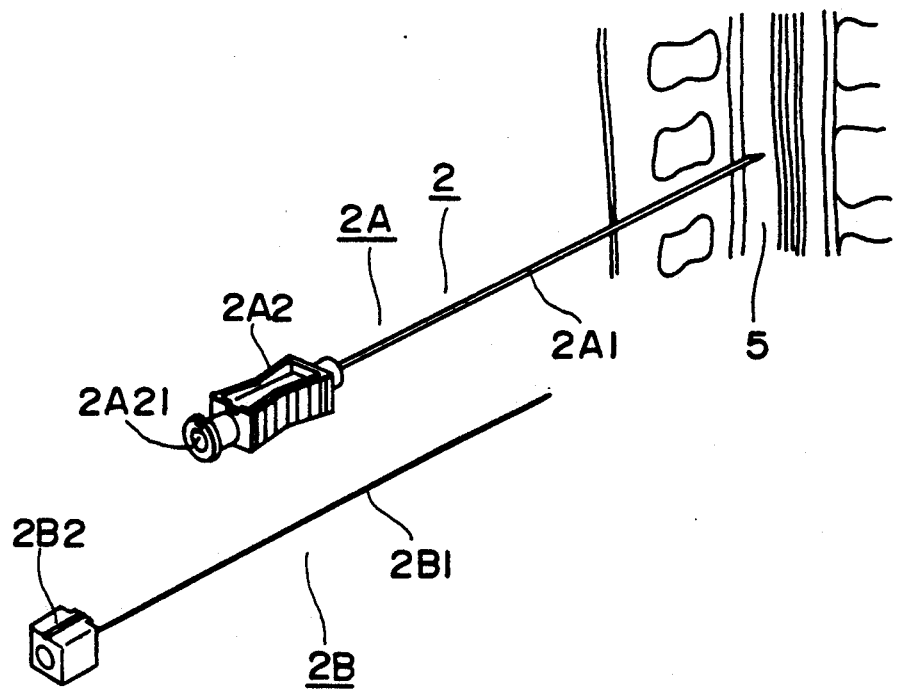
FIG. 2 is a perspective view illustrating a guide needle portion and a core portion separated from each other in the needle of FIG. 1.

An embodiment will now be described with reference to the drawings.

A reference numeral 1 denotes a continuous local anesthetization set consisting of a known puncturing guide needle 2, a guide member 3 and a catheter 4. The puncturing guide needle 2 consists of a guide needle portion 2A, and a core portion 2B capable of being inserted into and withdrawn from the guide needle portion 2A, and the guide needle portion 2A is composed of a guide needle 2A1 having an edge at the free end portion, and a receiving portion 2A2 attached to the base end of the guide needle 2A1, the core portion 2B being composed of a core 2B1 capable of being inserted into and withdrawn from the guide needle 2A1, and a knob 2B2 attached to the base end of the core 2B1, the knob being formed so that it is detachably fitted in a receiving bore 2A21 provided in the rear end surface of the receiving portion 2A2.

The guide member 3 consists of a guide pipe 3A, the diameter of which is substantially equal to that of the guide needle 2A1, and a knob 3B fitted firmly around a substantially intermediate portion of the outer circumferential surface of the guide pipe 3A, the knob 3B being provided on the surface thereof which is on the side of a front end 3A1 of the guide pipe 3A with a front end portion 3B1 adapted to be detachably fitted in the receiving bore 2A21. Referring to the drawings, a reference numeral 3A2 denotes the rear end of the guide pipe 3A.

The catheter 4 consists of, for example, a Teflon (trademark) tube, and is dimensioned so as to be moved forward and backward freely through the guide needle 2A1 and the guide pipe 3A, the catheter 4 being provided with a curled pigtail-like portion 4A at the front end section thereof. The pigtail-like portion 4A may consist of an inverted J-shaped bent portion 4A1. Referring to the drawings, a reference numeral 4B denotes the rear end of the catheter 4.

Figure 3:
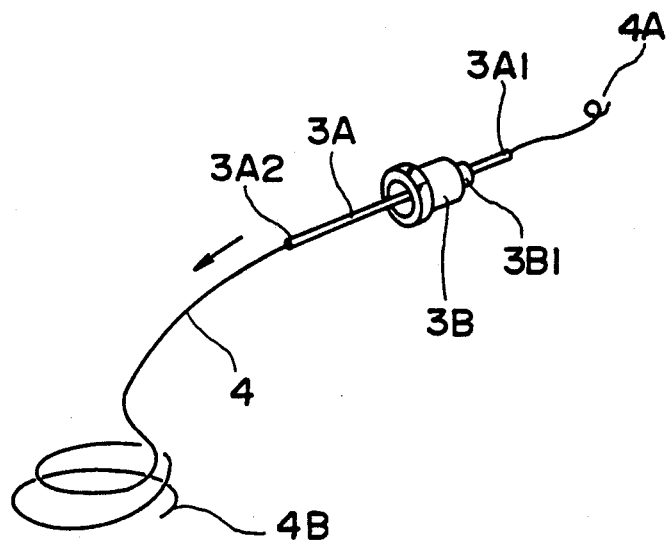
FIG. 3 is a perspective view illustrating a catheter inserted through a guide member.
Figure 4:
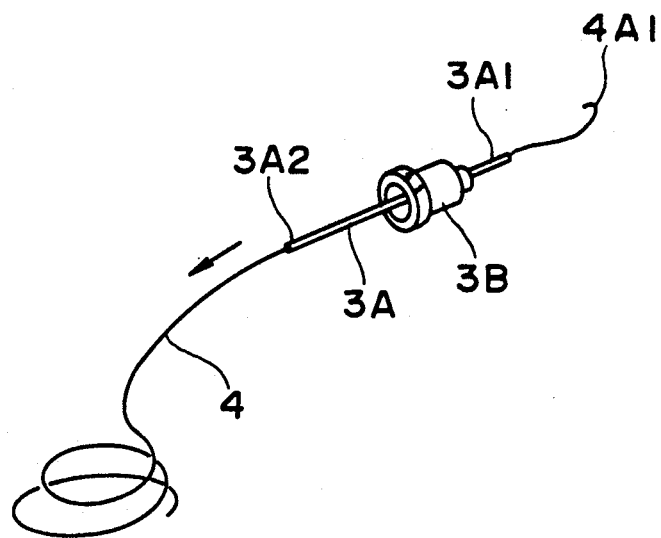
FIG. 4 is a perspective view illustrating a catheter inserted through a guide member.
Figure 5:
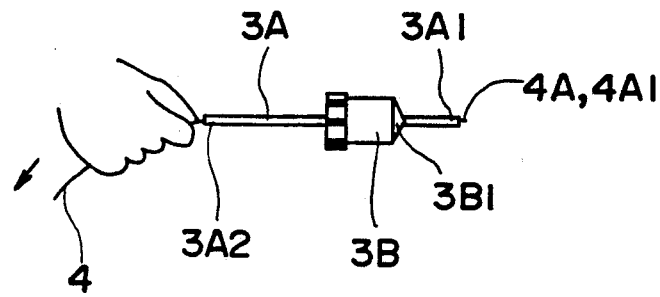
FIG. 5 is a side elevation illustrating a catheter inserted through a guide member.
Figure 7:
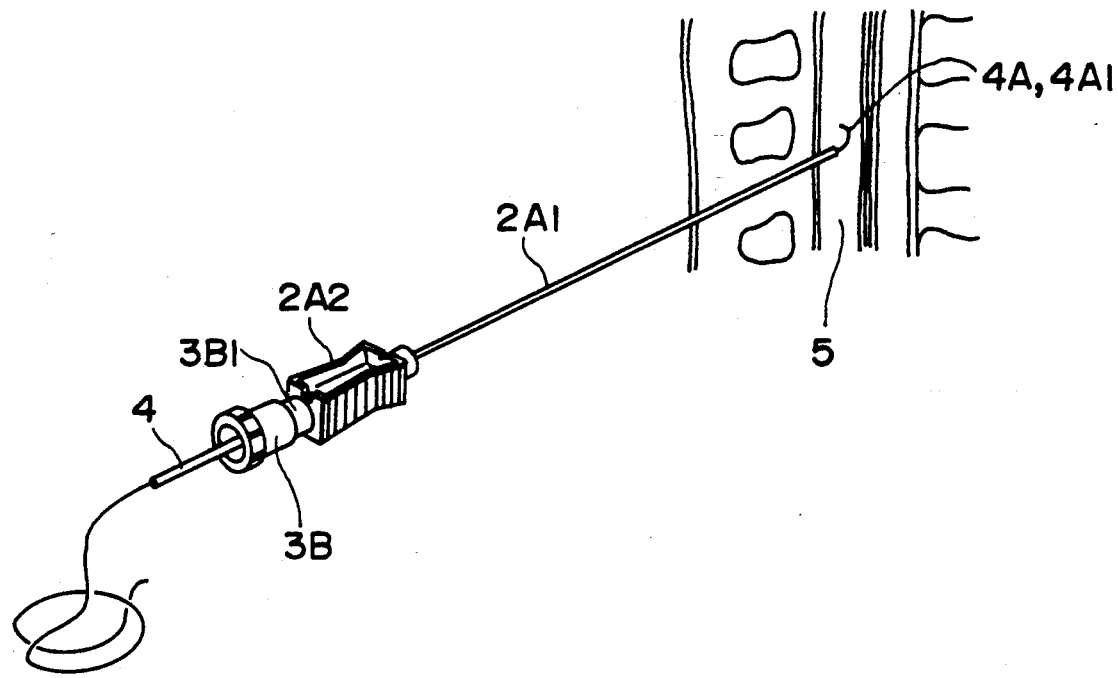
FIG. 7 is a perspective view showing the condition of an anesthetization set in use.
Figure 6:
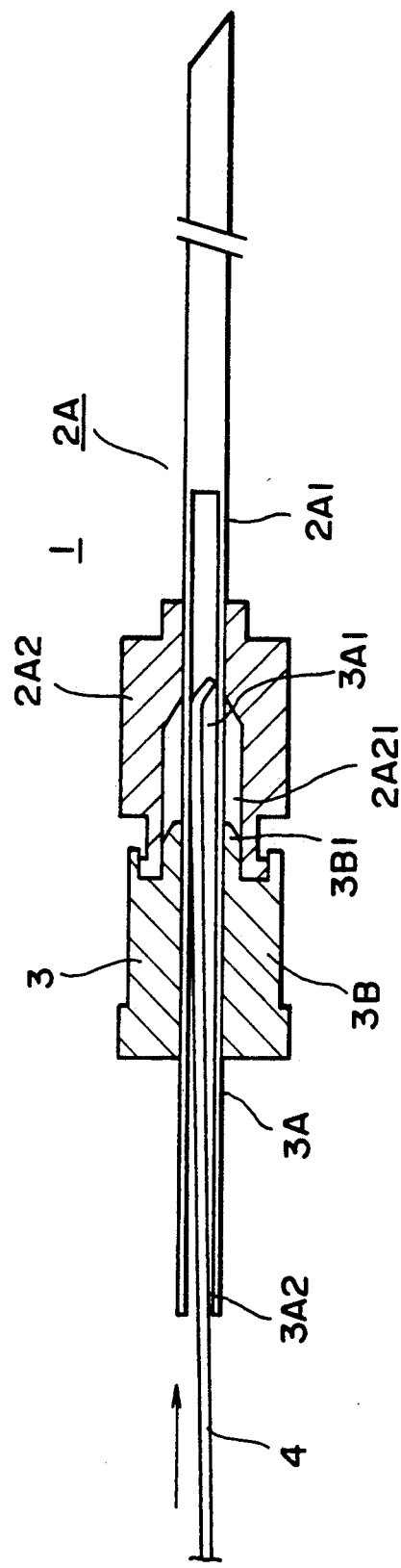
FIG. 6 is an enlarged longitudinal section showing the relation between the puncturing guide needle, guide member and catheter.
Figure 8:
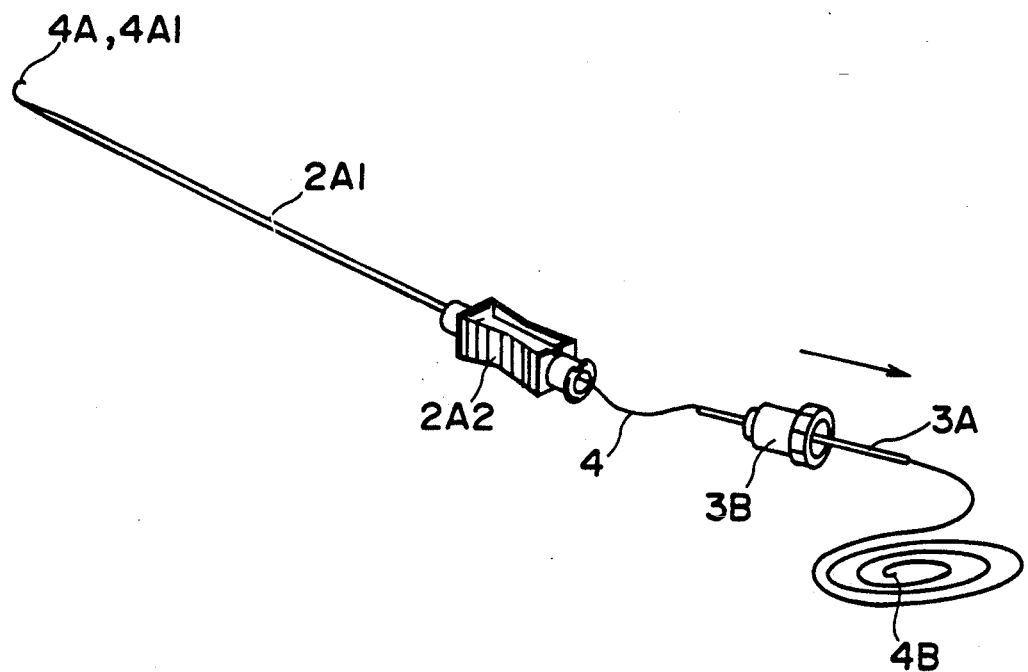
FIG. 8 is a perspective view showing the condition of the anesthetization set with the guide member being removed.
Figure 9:
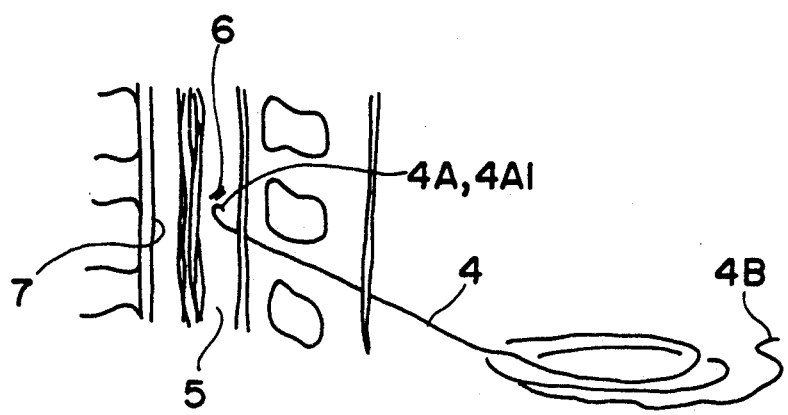
FIG. 9 is a perspective view of the catheter retained with its front end portion positioned in a spinal subarachnoid space.

The relation between the guide portion 3 and catheter 4 will now be described. As shown in FIGS. 3, 4 and 5, the catheter 4 is inserted at the rear end 4B thereof into the front end 3A1 of the guide pipe 3A in the guide member 3, passed through the guide pipe 3A and then drawn out therefrom gently, and the pigtail-like portion 4A or inverted J-shaped bent portion 4A1 is positioned in the front end portion 3A1 of the guide pipe 3A.

As a result, the pigtail-like portion 4A or inverted J-shaped bent portion 4A1 is retained forcibly in a straightened state in the front end portion 3A1 of the guide pipe 3A. Accordingly, when the pigtail-like portion 4A or inverted J-shaped bent portion 4A1 is stuck to the outside of the guide pipe 3A, it restores its original shape.

How to use the anesthetization set of the present invention will now be described.

A. The puncturing guide needle 2 is stuck into the skin so that the guide needle portion 2A reaches a spinal subarachnoid space 5.

B. The core portion 2B is pulled out to ascertain that the guide needle portion 2A has reached the spinal subarachnoid space with a medullary liquid flowing out.

C. The front end 3A1 of the guide pipe 3A in the guide member 3 is inserted into the receiving portion 2A2 of the puncturing guide needle 2, and the front end portion 3B1 of the guide member 3 and the receiving bore 2A21 in the receiving portion 2A2 are engaged with each other. Consequently, the guide pipe 3A and guide needle 2A1 are connected together linearly.

D. The catheter 4 is moved gently with the pigtail-like portion 4 or inverted J-shaped bent portion 4A1 at the head.

E. When the pigtail-like portion 4A or inverted J-shaped bent portion 4A1 projects beyond the front end of the guide needle portion 2A, i.e., into the spinal subarachnoid space, the pigtail-like portion 4A or inverted J-shaped bent portion 4A1 restores its original shape.

F. When the guide member 3 and puncturing guide needle 2 are moved back together gently and pulled out from the rear end of the catheter 4, the front end 4A1 of the catheter 4 is set firmly in a portion in the spinal subarachnoid space.

G. An anesthetic is injected into the rear end 4B of the catheter 4 by a known method. A reference numeral 6 denotes a portion, into which the anesthetic has permeated, around a spinal wall.

A reference numeral 7 denotes a spinal wall.

For example, when the blocking of a brachial plexus is done in a cervical region, the puncturing guide needle 2 is stuck perpendicularly into the portion of the skin which corresponds to a point, the height of which is equal to that of the lower edge of a cricoid cartilage, in a recess (inter-scalenal recess) between the scalenus anterior and scalenus medius. When the guide needle portion 2A passes through the connective tissue surrounding the brachial plexus, it meets with very weak resistance like the resistance encountered when a toothpick is put through the paper on a paper sliding door. After the guide needle portion 2A has met with such resistance, the tip of the needle 2A1 is advanced by about 5 mm and retained in the position.

The core portion 2B is drawn out from the guide needle portion 2A, and a local anesthetic is injected into the receiving bore 2A21. Consequently, a small space filled with the local anesthetic is formed between a membrane of connective tissue surrounding the brachial plexus and the same plexus.

The guide member 3 in which the pigtail-like portion 4A or inverted J-shaped bent portion 4A1 is set in the guide pipe 3A is then fitted in the receiving bore 2A21 in the guide needle 2A1. Since the guide pipe 3A and guide needle portion 2A become linear, the catheter 4 can be sent through the guide pipe 3A into the guide needle portion 2A. When the catheter 4 is further sent forward, the pigtail-like portion 4A or inverted J-shaped bent portion 4A1 in the guide needle portion 2A comes out from the front end of the guide needle 2A1. The front end portion 4A of the catheter 4 coming out of the guide needle 2A1 bends immediately to restore its original shape, so that the front end of the catheter 4 is not obstructed by the wall of the small space formed around the plexus and filled with a local anesthetic or a nerve. Accordingly, the front end of the catheter 4 can be set easily in the small space and positioned in the vicinity of a nerve.

As described above, the curled pigtail-like portion 4A or inverted J-shaped bent portion 4A1 of the catheter 4 can be inserted very easily into the puncturing guide needle 2 through the guide member 3, and the front end portion of the catheter 4 is curled at the moment it starts coming out from the edge of the puncturing guide needle 2. Accordingly, there is no possibility that the front end of the catheter 4 impinges upon the spinal wall, and the problem of partial injection of an anesthetic liquid and partial filling of an object space therewith is solved, so that a uniform anesthetization effect can be obtained.

What is claimed is:

1. A continuous local anesthetization set comprising a puncturing guide needle (2), a guide member (3), and a catheter (4), said puncturing guide needle (2) consisting of a guide needle portion (2A), and a core portion (2B) capable of being inserted into and withdrawn from said guide needle portion (2A), said guide needle portion (2A) being composed of a guide needle (2A1) having an edge at a free end thereof, and an inner and outer diameter, and a receiving portion (2A2) attached to a base end of said guide needle (2A1), said core portion consisting of a core (2B1) capable of being inserted into and withdrawn from a guide needle 23A1, and a knob (2B2) attached to the base end of said core (2B1), said knob being formed so that it is detachably fitted in a receiving bore (2A21) provided in the rear end surface of said receiving portion (2A2), said guide member (3) consisting of a guide pipe (3A) having an inner and outer diameter, the inner diameter of which is substantially equal to the inner diameter of said guide needle (2A1), said guide pipe (3A) linearally abutting said guide needle (2A1) such that there is no discontinuous space provided therebetween, and a knob (3B) fitted firmly around a substantially intermediate portion of an outer circumferential surface of said guide pipe (3A), said knob (3B) being provided on the surface thereof which is on the side of a front end (3A1) of said guide pipe (3A) with a front end portion (3B1) adapted to be detachably fitted in said receiving bore (2A21), said catheter (4) being dimensioned so as to be moved forward and backward freely through said guide needle (2A1) and said guide pipe (3A), said catheter (4) being provided at the front end section thereof with a curled pigtail-like portion (4A) or an inverted J-shaped bent portion (4A1).

* * * * *

UNITED STATES PATENT AND TRADEMARK OFFICE
CERTIFICATE OF CORRECTION

PATENT NO. :   5 263 936

DATED      :   November 23, 1993

INVENTOR(S):   Masaki Yurino

It is certified that error appears in the above-identified patent and that said Letters Patent is hereby corrected as shown below:

Column 5, line 16;  change "23A1" to ---2A1---.

Signed and Sealed this

Seventeenth Day of May, 1994

Attest:

BRUCE LEHMAN

*Attesting Officer*     Commissioner of Patents and Trademarks